United States Patent [19]

Keller et al.

[11] Patent Number: 4,883,900

[45] Date of Patent: Nov. 28, 1989

[54] PROCESS FOR THE PREPARATION OF ASPARTAME AND AGENTS FOR CARRYING IT OUT

[75] Inventors: Reinhold Keller, Bad Soden am Taunus; Merten Schlingmann, Königstein/Taunus; Martin Platen, Frankfurt am Main, all of Fed. Rep. of Germany

[73] Assignee: Hoechst Aktiengesellschaft, Frankfurt am Main, Fed. Rep. of Germany

[21] Appl. No.: 219,859

[22] Filed: Jul. 12, 1988

Related U.S. Application Data

[63] Continuation of Ser. No. 903,751, Sep. 5, 1986.

[30] Foreign Application Priority Data

Sep. 9, 1985 [DE] Fed. Rep. of Germany ....... 3532027

[51] Int. Cl.$^4$ ............................................ C07C 103/52
[52] U.S. Cl. ...................................................... 560/41
[58] Field of Search ........................................... 560/41

[56] References Cited

U.S. PATENT DOCUMENTS

| 3,941,831 | 3/1976 | Sollman | 260/471 A |
| 4,165,311 | 8/1979 | Isowa et al. | 435/68 |
| 4,256,836 | 2/1981 | Isowa et al. | 435/70 |
| 4,436,925 | 7/1984 | Isowa et al. | 560/19 |

FOREIGN PATENT DOCUMENTS

2801238  1/1978  Fed. Rep. of Germany.
61-27382 6/1986  Japan.

OTHER PUBLICATIONS

Morrison et al., *Organic Chemistry*, 3rd ed., Allyn and Bacon, Boston, 1973, pp. 682–683.

*Primary Examiner*—Bruce Gray
*Attorney, Agent, or Firm*—Finnegan, Henderson, Farabow, Garrett and Dunner

[57] ABSTRACT

Dipeptide alkyl esters whose alkyl group contains 3 to 7 carbon atoms can be converted to the corresponding methyl ester compound by a rapid, gentle transesterification in anhydrous methanol in the presence of an alkali metal alcoholate, without racemization occuring on the two chiral carbon atoms.

10 Claims, No Drawings

PROCESS FOR THE PREPARATION OF ASPARTAME AND AGENTS FOR CARRYING IT OUT

This application is a continuation of application Ser. No. 903,751, filed Sept. 5, 1986.

German Offenlegungsschrift 2,801,238 (U.S. Pat. Nos. 4,165,311, 4,256,836 and 4,436,925), describes a process for the preparation of addition compounds which comprise, on the one hand, an N-protected monoaminocarboxylate and, on the other hand, a dipeptide, the dipeptide itself having been prepared from this monoaminocarboxylate and a monoaminodicarboxylate in an enzymatic esterification reaction. The addition compound is insoluble in the reaction medium and is separated off. However, the actual aim of this transesterification is not the preparation of the addition compound, but instead that of the unprotected dipeptide itself. Several methods which involve the formation of the dipeptide by decomposition of the addition compound are described in the literature, including in the above-mentioned German Offenlegungsschrift.

In practice, the process is used, for example, in the preparation of the sweetener aspartame, a dipeptide ester, which is prepared from aspartic acid and methyl D/L-phenyl-alanate as starting compounds. The aspartic acid is linked enzymatically to the methyl L-phenylalanate, while excess methyl D-phenylalanate adds to the dipeptide for adduct formation. The methyl aspartylphenylalanate is liberated from the adduct in a further reaction step.

However, it has surprisingly been shown that the enzymatic linking to higher alkyl esters than the methyl or ethyl esters of D/L-phenylalanate brings about significant advantages in the further processing.

In addition, it has been found that the corresponding dipeptide alkyl esters of the higher alcohols can be converted quantitatively to the desired methyl ester compound by a rapid, gentle transesterification in anhydrous methanolic medium in the presence of basic catalysts, such as, for example, alkanolates or anion exchangers, without a racemization occurring on the two chiral carbon atoms under these conditions. This was particularly surprising since the racemization of optically active α-amino acid alkyl esters under the same conditions is described in published Japanese Patent Application 79/84,522.

The invention thus relates to:

1. A process for the preparation of the compound of the general formula III

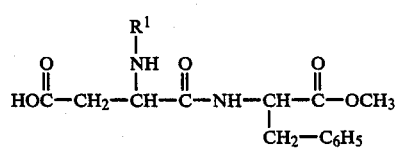

in which $R^1$ is an amino-protecting group, which comprises transesterifying the compound of the general formula II,

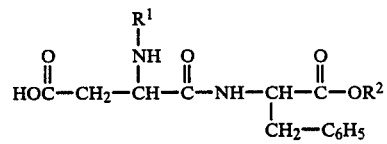

in which
$R^1$ denotes an amino-protecting group and
$R^2$ denotes an alkyl group having 3–7 carbon atoms,
in anhydrous methanol.

2. The compound of the general formula II

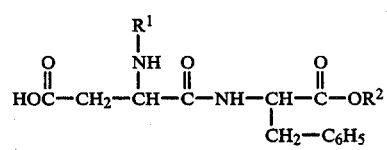

in which
$R^1$ denotes an amino-protecting group and
$R^2$ denotes an alkyl group having 3–7 carbon atoms.

3. The addition compound of the general formula I,

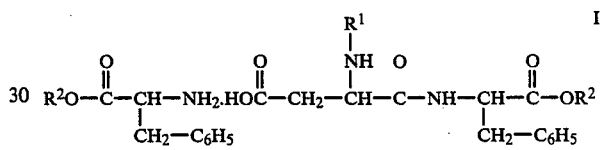

in which
$R^1$ denotes an amino-protecting group and
$R^2$ denotes an alkyl group having 3–7 carbon atoms.

4. A process for the preparation of the addition compound of the general formula I, in which $R^1$ is an amino-protecting group and $R^2$ is an alkyl group, by linking of an N-protected aspartic acid to an alkyl D/L-phenylalanate or alkyl L-phenylalanate in the presence of a protease, in a pH range in which the protease is enzymatically active, wherein the alkyl group of the alkyl D/L-phenylalanate used has 3–7 carbon atoms.

5. A process for the preparation of the compound of the general formula II, in which $R^1$ is an amino-protecting group and $R^2$ is an alkyl group, by decomposition of the addition compound of the general formula I, in which $R^1$ and $R^2$ have the abovementioned meaning, in an aqueous acidic solution, wherein $R^1$ in the addition compound of the general formula I used has the abovementioned meaning and $R^2$ denotes an alkyl group having 3–7 carbon atoms.

In the general formulae I, II and III, $R^1$ is an amino-protecting group, a protecting group of the urethane type being preferred, particularly a benzyloxycarbonyl group or a tertiary butyloxycarbonyl group. In the formulae I and II, $R^2$ is an alkyl group having 3–7 carbon atoms, n-propyl, iso-propyl, n-butyl and n-pentyl being particularly preferred groups.

The preparation of the addition compound of the general formula I and the liberation of the compound of the general formula II from this addition compound occurs analogously to German Offenlegungsschrift 2,801,238. The N-protected L-aspartic acid is reacted with an alkyl D/L-phenylalanate or alkyl L-phenylalanate whose alkyl group has 3–7 carbon atoms, in aqueous medium using a protease to form the compound of the general formula II, which links to the excess alkyl phenylalanate under the reaction conditions to form the addition compound of the general formula I, which then precipitates and can be separated off. Unpurified thermolysine is preferably employed as protease. The reaction proceeds advantageously in aqueous solution at a pH of 5.0–6.0, the N-protected aspartic acid being initially introduced together with the enzyme, and the alkyl D/L-phenyalanate being metered in in the course of the reaction in the form of a concentrated aqueous solution. The metered addition of a highly concentrated aqueous solution of N-protected aspartic acid and alkyl D/L-phenylalanate into an aqueous initial charge of enzyme is likewise advantageous.

A further possibility for the preparation of an addition compound is proposed in Patent Application P 3,517,361.0. The compound of the formula II reacts with an amine present in the reaction mixture to form the adduct.

The compound of the general formula II is liberated from the addition compound according to the invention in aqueous medium by addition of a strong acid, preferably hydrochloric acid. The alkyl phenylalanate likewise liberated in the course of the addition can be extracted from aqueous alkaline solution using an organic solvent, preferably diethyl ether, and subsequently precipitated as the hydrochloride by introduction of gaseous hydrochloric acid.

The use of the $(C_3-C_7)$-alkyl ester compounds has the following advantages compared to the lower homologues: The $(C_3-C_7)$-alkyl D/L-phenylalanate or the corresponding L compound displays a greater stability to chemical hydrolysis. The corresponding addition compound is easier to separate from the reaction mixture. After cleavage of the adduct, the $(C_3-C_7)$-alkyl D/L-phenylalanates or the corresponding L compound can be recovered more simply and in quantitative yield.

The compound of the general formula II must be transesterified to form the corresponding methyl ester at the end of the reaction sequence described, in order to obtain aspartame.

For the transesterification, the dipeptide ester is dissolved in andhydrous methanol, with addition of an alkali metal alcoholate as catalyst. When the reaction is carried out in the presence of sodium methanolate or potassium methanolate, the transesterification proceeds particularly advantageously. The catalyst is employed in 1 to 5 times the molar amount, relative to the dipeptide ester. However, 1.1 to 2 times the molar amount is preferred. The reaction proceeds at a temperature of −20° C. to 50° C., preferably at 0° C. to 40° C., particularly at 18° C. to 25° C. The reaction duration is only 10 to 15 minutes when using the particularly preferred temperature range. Carrying out the reaction at a relatively low temperature, such as, for example, at room temperature has the advantage that not only is energy saved but also that side reactions are suppressed. In order to isolate the dipeptide methyl ester, compound of general formula I it can be introduced into an acid after concentrating the reaction solution and subsequently be crystallized from a suitable solvent.

The following examples give a further detailed description of the invention. The percentages are by weight.

EXAMPLE 1

Preparation of N-protected propyl L-aspartylphenylalanate adduct 53.0 g (0.2 mol) of L-N-benzyloxycarbonylaspartic acid and 1 g of calcium acetate are dissolved in 150 ml of distilled water and the pH of the solution is adjusted to 5.8 using 5N sodium hydroxide solution. 5.0 g of crude thermolysine (DAIWA KASEI K.K. Thermoase SP 160) are then added. The temperature of the solution is maintained at 40° C. under thermostat control and 121.5 g (0.5 mol) of propyl D/L-phenylalanate hydrochloride which are dissolved in 100 ml of distilled water are added with stirring over a period of 5 h during, which the pH of the solution is maintained at 5.8 by addition of 5N sodium hydroxide solution. After 8 h, the precipitated product is filtered off and washed with 500 ml of distilled water, and the crystals are dried in a drying cabinet at 70° C.

126 g of adduct (95% relative to the N-protected aspartic acid employed) are obtained.

Melting point: 134°–136° C.

Optical rotation: $[\alpha]^{25}_D$: −8.4 (1 c in methanol)

$^1$H NMR (100 MHz, DMSO-d$_6$): 7.4–7.0 (15H); 6.2–6.0 (5H); 5.05 (2H); 4.85–4.40 (2H); 4.10–3.85 (5H); 3.20–2.50 (6H); 1.85–1.45 (4H); 1.00–0.75 (6H).

EXAMPLE 2

53.0 g (0.2 mol) of L-N-benzyloxycarbonyl aspartic acid and 109 g (0.45 mol) of propyl D/L-phenylalanate hydrochloride which are dissolved in 200 ml of distilled water are added dropwise in the course of 6 h to a solution of 1 g of calcium acetate and 5.0 g of Thermoase SP 160 in 100 ml of distilled water. The reaction temperature is 40° C. The pH of the solution is maintained at 5.8 during the reaction by addition of 5N sodium hydroxide solution. After a reaction time of 8 h, the precipitated adduct is filtered off and washed with 300 ml of water.

113 g of adduct (85% relative to the N-protected aspartic acid employed) are obtained.

EXAMPLE 3

Preparation of N-protected butyl L-aspartylphenylalanate adduct.

The procedure according to Example 1 or 2 is carried out, except that butyl D/L-phenylalanate hydrochloride is employed. The yields are analogous to the examples mentioned.

Melting point: 124°–128° C.

Optical rotation: $[\alpha]^{25}_D$: −4.2 (1 c in methanol)

EXAMPLE 4

Preparation of N-protected propyl L-aspartylphenylalanate.

107 g (0.161 mol) of the adduct obtained from Example 1 or 2 are taken up in 1 liter of 2N hydrochloric acid and stirred vigorously for 30 min at room temperature. The precipitated product is filtered off, washed thoroughly with distilled water and dried in the drying cabinet at 80° C.

72 g (98.0% of theory) of N-protected propyl L-aspartylphenylalanate are obtained.

Melting point: 118° C.

Optical rotation: $[\alpha]^{25}_D$: −17.0 (1 c in methanol)

$^1$H NMR (100 MHz, DMSO-d$_6$) 8.25–8.15 (1H); 7.50–7.40 (1H); 7.30–7.15 (15H); 4.97 (2H); 4.60–4.10 (2H); 3.96–3.80 (2H); 3.45–3.25 (2H); 3.05–2.95 (2H); 1.65–1.20 (4H); 0.85–0.70; (3H).

EXAMPLE 5

Preparation of N-protected butyl L-aspartyl-phenylalanate.

The procedure according to Example 4 is carried out, except that the adduct obtained from Example 3 is employed. The yields are analogous to Example 4.

Melting point: 112° C.

Optical rotation: $[\alpha]^{25}_D$: −16.5 (1 c in methanol)

EXAMPLE 6

Recovery of the propyl phenylalanate.

The aqueous filtrate obtained from Example 4 is adjusted to pH 8.0 using 5N NaOH. The propyl ester is extracted with diethyl ether. After drying the organic phase the propyl ester is precipitated as the hydrochloride by introduction of gaseous hydrochloric acid.

33.0 g (84% of theory) of propyl phenylalanate hydrochloride are obtained.

EXAMPLE 7

Transesterification of N-protected propyl L-aspartyl-phenylalanate.

84 g (0.18 mol) of the product obtained from Example 4 are dissolved in 840 ml of anhydrous methanol, which has been distilled over magnesium, and 50 ml of 30% strength methanolic sodium methanolate solution (0.28 mol) are added with stirring. After 17 min at room temperature, the reaction has proceeded fully to completion, as can be monitored using an HPLC instrument. 60 ml (0.3 mol) of glacial acetic acid are added to this mixture and the solution is concentrated on a rotary evaporator. The oily residue is brought to crystallization in ethyl acetate/n-hexane [4/1 (vol/vol)].

Yield: 77.0 g of N-protected methyl L-aspartyl-phenylalanate.

The optical rotation: $[\alpha]^{25}_D$: −14.7; (1 c in methanol)

EXAMPLE 8

The procedure according to Example 7 is carried out at 5° C. After 4 h, the reaction has proceeded fully to completion with analogous results as in Example 7.

We claim:

1. A process for the preparation of an optically active form of the compound of the formula III

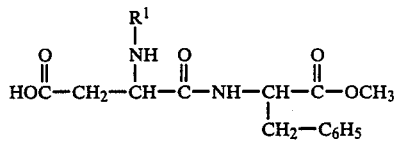

in which $R_1$ is an amino-protecting group, without a racemization occurring on the two chiral carbon atoms under the reaction conditions, which process comprises dissolving the optically active compound of the formula II

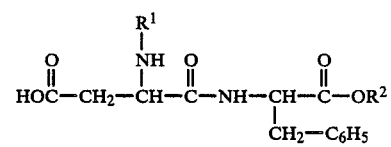

in which $R^1$ is an amino-protecting group and $R^2$ is an alkyl group having 3–7 carbon atoms, in anhydrous methanol, and transesterifying said compound at a temperature of −20° to 50° C. with the addition of an alkali metal alcoholate.

2. The process as claimed in claim 1, wherein $R^1$ is an amino-protecting group of the urethane type.

3. The process as claimed in claim 2, wherein $R^1$ is a benzyloxycarbonyl group or a tertiary butyloxycarbonyl group.

4. The process as claimed in claim 1, wherein $R^2$ is an n-propyl, iso-propyl, n-butyl or n-pentyl group.

5. The process as claimed in claim 1, wherein the reaction is carried out with addition of alkali metal methanolate.

6. The process as claimed in claim 5, wherein the reaction is carried out with addition of sodium methanolate.

7. The process as claimed in claim 1, wherein the alkali metal alcoholate is employed in 1.0 to 5 times the molar amount, relative to the compound of the formula II.

8. The process as claimed in claim 7, wherein the alkali metal alcoholate is employed in 1.1 to 2.0 times the molar amount.

9. The process as claimed in claim 1, wherein the reaction is carried out at −20° to 30° C.

10. The process as claimed in claim 9, wherein the reaction is carried out at 18° to 25° C.

* * * * *